US011266756B2

(12) United States Patent
Robincheck et al.

(10) Patent No.: US 11,266,756 B2
(45) Date of Patent: Mar. 8, 2022

(54) SYSTEM AND METHOD FOR BACTERIA IRRADIATION FROM AN OCCUPANT ZONE OF A VEHICLE

(71) Applicant: GM Global Technology Operations LLC, Detroit, MI (US)

(72) Inventors: Janet C. Robincheck, Sterling Heights, MI (US); Adam F. Gross, Santa Monica, CA (US); Nancy L. Johnson, Northville, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 199 days.

(21) Appl. No.: 16/528,038

(22) Filed: Jul. 31, 2019

(65) Prior Publication Data
US 2021/0030904 A1 Feb. 4, 2021

(51) Int. Cl.
| | |
|---|---|
| *A61L 2/08* | (2006.01) |
| *A61L 2/10* | (2006.01) |
| *A61L 2/26* | (2006.01) |
| *B60S 1/64* | (2006.01) |
| *B60Q 3/00* | (2017.01) |

(52) U.S. Cl.
CPC ............ *A61L 2/084* (2013.01); *A61L 2202/11* (2013.01); *A61L 2202/14* (2013.01)

(58) Field of Classification Search
None
See application file for complete search history.

(56) References Cited

U.S. PATENT DOCUMENTS

| | | | |
|---|---|---|---|
| 8,232,533 B2 * | 7/2012 | Kingsley ............... | C09K 11/06 250/459.1 |
| 2015/0137747 A1 * | 5/2015 | Salter ..................... | B60N 3/14 320/108 |

(Continued)

FOREIGN PATENT DOCUMENTS

JP 5075782 B2 * 11/2012

OTHER PUBLICATIONS

McCudden et al, Britannica Student Encyclopedia, vol. 1, 2015, Encyclopedia Britannica, Inc., (Year: 2015).*

(Continued)

*Primary Examiner* — Holly Kipouros
(74) *Attorney, Agent, or Firm* — Vivacqua Crane PLLC

(57) ABSTRACT

A system for bacteria irradiation from an occupant zone of a vehicle is provided. The system comprises an interior portion disposed in the occupant zone. The interior portion has one of a predetermined surface porosity and a predetermined surface roughness. The interior portion has phosphorescent paint for visual indication. The system further comprises a high energy visible (HEV) light source integrated within the interior portion. The HEV light source has an emission wavelength of between about 375 nm and about 425 nm. The HEV light source further provides a cumulative energy of between about 1 $J/cm^2$ and about 50 $J/cm^2$. The system further comprises a vehicle processor in communication with the HEV light source. The vehicle processor is configured to enable the HEV light source. The system further comprises a sensor in communication with the vehicle processor and configured to provide input on when to enable light source.

14 Claims, 2 Drawing Sheets

(56) References Cited

U.S. PATENT DOCUMENTS

2015/0273093 A1* 10/2015 Holub .................. B60Q 3/20
                                                    250/492.1
2019/0167833 A1*  6/2019 Yang ..................... F24F 8/10
2020/0360549 A1* 11/2020 Neveu ................. A61B 50/33

OTHER PUBLICATIONS

Sinclair et al., Textiles and Fashion, 2015, Woodhead Publishing Limited, 2015 (Year: 2015).*
English Machine Translation of JP 5075782 B2 provided by Espacenet (Year: 2012).*
Mustang America Catalog, Mustang America, publicly available as of Jun. 2, 2019 (see Wayback Machine cache screenshot appended to beginning of document) (Year: 2019).*

* cited by examiner

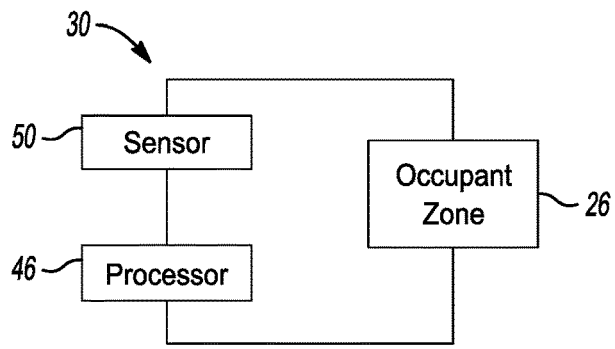
FIG. 2
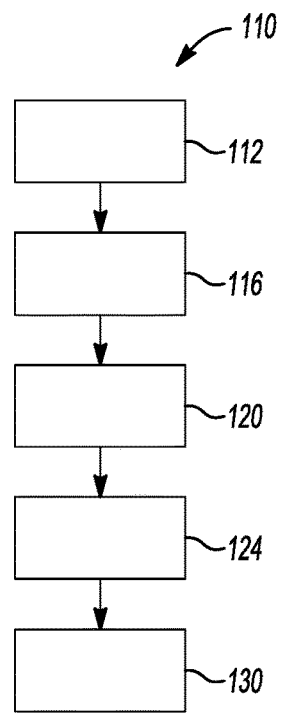
FIG. 3
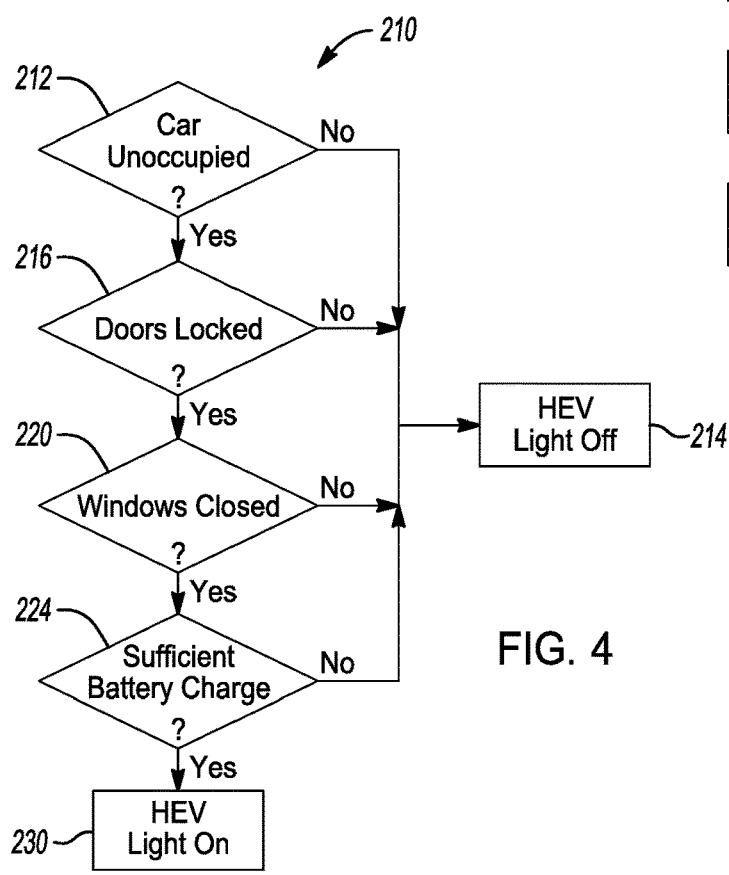
FIG. 4
| Surfaces | TPO | Painted PP | Leather | Fabric | Vinyl |
|---|---|---|---|---|---|
| Reduction after 5 J/cm$^2$ | 68% | 75% | 71% | 71% | 51% |
| Reduction after 20 J/cm$^2$ | 79% | 93% | 90% | 86% | 84% |
| Reduction after 40 J/cm$^2$ | 94% | 95% | 94% | 47% | 91% |
FIG. 5

SYSTEM AND METHOD FOR BACTERIA IRRADIATION FROM AN OCCUPANT ZONE OF A VEHICLE

INTRODUCTION

The present disclosure relates to systems and methods of irradiating bacteria. More particularly, the present disclosure relates to systems and methods of irradiating bacteria from an occupant zone of a vehicle.

Undesirable organisms, such as bacteria, viruses, fungi, and molds are health hazards. As technology advances, the age of the average vehicle continues to rise. Currently the average age of all cars on the road is more than 11 years, up from 8.4 years in 1995. As such, the interior of the average vehicle is vulnerable to bacterial growth therein. An increasing concern involves continual growth of such organisms and their residue in vehicles.

SUMMARY

Thus, there is a need for a new and improved system and method for reducing bacteria from an occupant zone of a vehicle.

According to one embodiment of the present disclosure, a system for bacteria irradiation from an occupant zone of a vehicle is provided. The system comprises an interior portion disposed in the occupant zone. The interior portion may include an instrument panel, door trim, seating, a headliner, an overhead trim, consoles, cargo trim, steering wheel, flooring systems, displays, buttons, switches, and various other interior trim panels.

Moreover, the interior portion has one of a predetermined surface porosity and a predetermined surface roughness. In one embodiment, the interior portion has a surface porosity of at least about 1 volume percent. In another embodiment, the interior portion has surface porosity of at least about 0.5 area percent. In yet another embodiment, the interior portion has a surface roughness of at least 10 microns Ra. Moreover, the interior portion has phosphorescent paint for visual indication of bacteria irradiation.

The system further comprises a high energy visible (HEV) light source integrated within the interior portion. The HEV light source has an emission wavelength of between about 375 nm and about 425 nm. Moreover, the HEV light source provides a cumulative energy of between about 1 J/cm$^2$ and about 50 J/cm$^2$ on surfaces in the vehicle. In one embodiment, the HEV light source is a light-emitting diode. In another embodiment, the emission wavelength of the HEV light source provides between about 390 nm and about 410 nm. In yet another embodiment, the emission wavelength of the HEV light source is between about 400 nm and about 405 nm.

The cumulative energy of the HEV light source may be between about 5 J/cm$^2$ and about 40 J/cm$^2$. In another embodiment, the cumulative energy of the HEV light source may provide between about 5 J/cm$^2$ and about 40 J/cm$^2$. In yet another embodiment, the cumulative energy of the HEV light source may be about 20 J/cm$^2$.

The system further comprises a vehicle processor in communication with the HEV light source. The vehicle processor is configured to enable the HEV light source. Moreover, the system comprises a sensor in communication with the vehicle processor and configured to provide input on when to enable light source. Furthermore, the sensor includes a motion sensor, a mass sensor, an ultrasonic sensor, a pressure sensor, an optical sensor, a light sensor, a temperature sensor, and an infrared sensor.

In another aspect of the present disclosure, a vehicle having a system for bacteria irradiation is provided. The vehicle comprises a chassis and a body supported by the chassis. The body includes a motor compartment and an occupant zone.

In this aspect, the vehicle comprises a system for bacteria irradiation from the occupant zone. The system comprises an interior portion disposed in the occupant zone. The interior portion may include an instrument panel, door trim, seating, a headliner, an overhead trim, consoles, cargo trim, steering wheel, flooring systems, displays, buttons, switches, and various other interior trim panels.

In one embodiment, the interior portion has a surface porosity of at least about 1 volume percent and a surface roughness of at least 10 microns Ra. In yet another embodiment, the interior portion has surface porosity of at least about 0.5 area percent. The interior portion further has phosphorescent paint for visual indication of bacteria irradiation.

The system further comprises a high energy visible (HEV) light source integrated within the interior portion. In this aspect, the HEV light source is a light-emitting diode and has an emission wavelength of between about 390 nm and about 410 nm. In another embodiment, the emission wavelength of the HEV light source is between about 400 nm and about 405 nm. Moreover, the HEV light source provides a cumulative energy of between about 5 J/cm$^2$ and about 40 J/cm$^2$. In another embodiment, the cumulative energy of the HEV light source is about 20 J/cm$^2$.

In this aspect, the system further comprises a vehicle processor in communication with the HEV light source. The vehicle processor configured to enable the HEV light source. Moreover, the system further comprises a sensor in communication with the vehicle processor and configured to provide input on when to enable light source. The sensor may include a motion sensor, a mass sensor, an ultrasonic sensor, a pressure sensor, an optical sensor, a light sensor, a temperature sensor, and an infrared sensor.

In another aspect, a method of irradiating bacteria from an occupant zone of a vehicle is provided. The method comprises providing an interior portion disposed in the occupant zone. In this example, the interior portion has a surface porosity of at least about 1 volume percent and a surface roughness of at least 10 microns Ra. Moreover, the interior portion having phosphorescent paint for visual indication.

The method further comprises sensing the occupant zone to determine whether the occupant zone is unoccupied.

The method further comprises enabling a high energy visible (HEV) light source, if the occupant zone is determined to be unoccupied. In this example, the HEV light source is integrated within the interior portion. Moreover, the HEV light source may have an emission wavelength of between about 375 nm and about 425 nm. Furthermore, the HEV light source provides a cumulative energy of between about 1 J/cm$^2$ and about 50 J/cm$^2$.

In one example, the HEV light source provides an emission wavelength of between about 390 nm and 410 nm. In another example, the HEV light source provides a cumulative energy of between about 5 J/cm$^2$ and about 40 J/cm$^2$.

The method further comprises exposing the HEV light source on the interior portion to irradiate bacteria from the occupant zone. The method then comprises exciting or reacting phosphorescent paint to HEV light source to indicate exposure of HEV light source in occupant zone. The phosphorescent paint contains a pigment that is sensitive to blue light but not the broad visible spectrum. The pigment may primarily absorb light <450 nm, <425 nm, or <400 nm based on the composition. Examples of pigments in phosphorescent paint are zinc sulfide, strontium aluminate, doped strontium aluminate, calcium sulfide, and alkaline earth metal silicate.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

FIG. 2 is schematic diagram of the system for bacteria irradiation of FIG. 1.

FIG. 3 is a flowchart of a method for bacteria irradiation from an occupant zone of FIG. 1 in accordance with one example of the present disclosure.

FIG. 4 is a flowchart of a control algorithm for enabling/disabling an HEV light source of the system in FIG. 1.

FIG. 5 is a table depicting bacteria reduction data of surfaces exposed by selected cumulative energy of a high energy light source.

DETAILED DESCRIPTION

Figure 1:
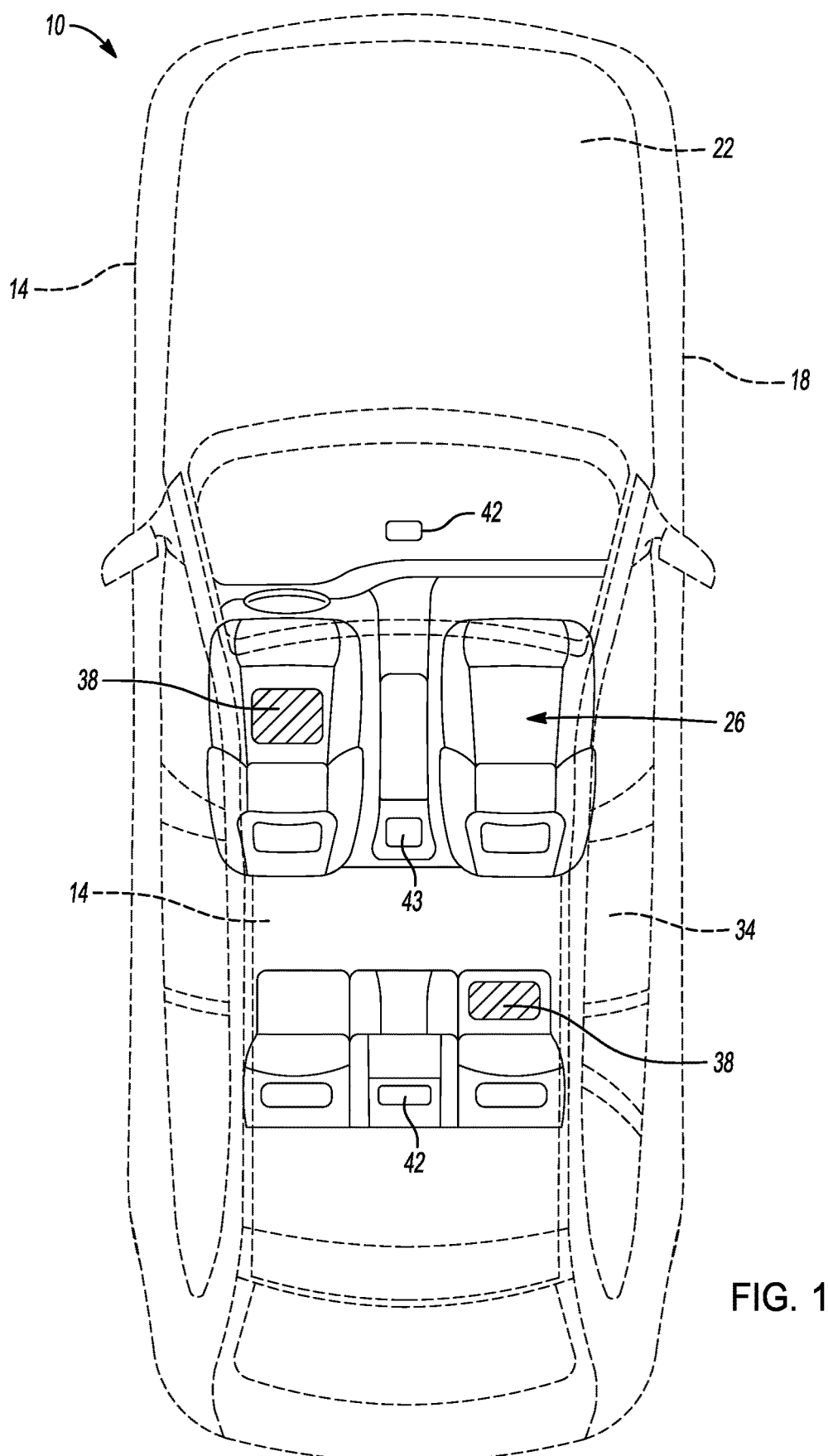
FIG. 1 is a plan view of a vehicle having a system for bacteria irradiation from an occupant zone of the vehicle in accordance with one embodiment of the present disclosure.

The following description is merely exemplary in nature and is not intended to limit the present disclosure, application, or uses.

According to one embodiment of the present disclosure, FIG. 1 illustrates a vehicle 10 comprising a chassis 14 and a body 18 supported by the chassis 14. As shown, the body 18 includes a motor compartment 22 and an occupant zone 26. The vehicle further includes a system 30 for bacteria irradiation from the occupant zone 26.

Referring to FIGS. 1-2, the system 30 comprises an interior portion 34 disposed in the occupant zone 26 of the vehicle 10. It is to be understood that the interior portion 34 may include a number of components within the occupant zone 26. For example, the interior portion 34 may include an instrument panel, door trim, seating, a headliner, an overhead trim, consoles, cargo trim, steering wheel, flooring systems, displays, buttons, switches, various other interior trim panels or any other suitable component in the occupant zone of the vehicle without departing from the spirit of the present disclosure.

Preferably, the interior portion 34 has one of a predetermined surface porosity and a predetermined surface roughness. Surfaces of the interior portion may include leather, cloth, fabric, polymeric material or any other suitable material without departing from the spirit of the present disclosure. It is to be understood that surface porosity may be defined or measured by way of volume percent or area percent. For example, the interior portion 34 may have a surface porosity of at least about 1 volume percent.

In another embodiment, the interior portion may have a surface porosity of about 0.5 area percent. It is understood that area percent is the amount a free space that can be viewed through fabric, normal to the surface. In another embodiment, the interior portion may have between about 5% and about 40% surface area greater than a flat surface. In yet another embodiment, the interior portion 34 may have a surface roughness (Ra) of at least 10 microns and up to about 1 mm.

Moreover, the interior portion 34 comprises phosphorescent paint 38 for visual indication of bacteria irradiation. As will be discussed in greater detail below, phosphorescent paint 38 is preferably disposed or integrated anywhere within the surface of the interior portion 34, e.g., an armrest or a seat, as a visual cue to an occupant of the vehicle 10, indicating that bacteria has been irradiated/reduced from the interior portion 34.

As shown, the system 30 further comprises a high energy visible (HEV) light source 42 integrated within the interior portion 34. Preferably, the system comprises a plurality of HEV light sources mounted within the occupant zone 26. In this embodiment, the HEV light source 42 is a light-emitting diode (LED). The LED may be mounted onto the interior portion 34 such as an overhead panel or other trim parts in the occupant zone 26 of the vehicle 10. It is to be understood that the LED may be mounted to any suitable component within the occupant zone 26 such as an instrument panel, door trim, seating, a headliner, an overhead trim, consoles, cargo trim, steering wheel, flooring systems, displays, buttons, switches, and various other interior trim panels without departing from the spirit of the present disclosure. The LED is preferably mounted flush with any surface of the interior portion 34 and also behind a transparent cover. For knitted surfaces or seats, the LED may be integrated into the fabric allowing for more uniform exposure. Additionally, the LED may be disposed inside a vehicle seat or headliner (e.g. knit or woven thereon) or coupled to an optical fiber of an upholstery of the vehicle.

In another example, the LED may be mounted to a portable device 43 which may be placed inside the occupant zone. Such portable device 43 may include a handheld device. Accordingly, the LED may be operated remotely or by wired connection.

In this embodiment, the HEV light source has an emission wavelength of between about 375 nm and about 425 nm of visible light. Preferably, the HEV light source 42 emits blue light wavelengths of a visible light spectrum. In another embodiment, the emission wavelength of the HEV light source 42 is between about 390 nm and about 410 nm. In yet another embodiment, the emission wavelength of the HEV light source 42 is between about 400 nm and about 405 nm of visible light.

Preferably, the HEV light source 42 provides a cumulative energy of between about 1 J/cm$^2$ and about 50 J/cm$^2$. In another embodiment, the cumulative energy of the HEV light source 42 may be between about 5 J/cm$^2$ and about 40 J/cm$^2$. In yet another embodiment, the cumulative energy of the HEV light source 42 may be about between about 10 J/cm$^2$ and about 30 J/cm$^2$. In still another example, the cumulative energy of the HEV light source 42 may be about 20 J/cm$^2$.

As shown in FIGS. 1 and 2, the system 30 further comprises a vehicle processor 46 in communication with the HEV light source 42. The vehicle processor 46 is in communication (wired or wireless) with the HEV light source 42 by any suitable manner and is configured to enable/disable the HEV light source 42 in the occupant zone 26 of the vehicle 10. As will be discussed in greater detail below, the processor 46 may include at least one algorithm in processing steps to enable or disable the HEV light source 42 in the occupant zone 26.

Moreover, the system 30 comprises a sensor 50 in communication with the vehicle processor 46 for providing input as to the occupancy status within the occupant zone 26. Preferably, the system 30 comprises a plurality of sensors 50 mounted within the occupant zone. In this embodiment, the sensor 50 is in communication (wired or wireless) with the processor 46 by any suitable manner to provide data input to the processor 46 regarding the occupancy status within the occupant zone 26. Such input to the processor 46 is used by the processor to enable or disable the HEV light source 42 on the interior portion 34.

It is to be understood that the sensor 50 may be any suitable sensor that may provide such input to the processor 46 to enable or disable the HEV light source 42 in the occupant zone 26. For example, the sensor 50 may include a motion sensor, a mass sensor, an ultrasonic sensor, a pressure sensor, an optical sensor, a light sensor, a temperature sensor, and an infrared sensor, or any other suitable sensor without departing from the spirit of the disclosure.

Referring to FIG. 3, a method 110 of irradiating bacteria from an occupant zone 26 of the vehicle 10 (FIG. 1) is provided. The method 110 comprises a step 112 of providing the interior portion 34 disposed in the occupant zone 26. In one example, the interior portion 34 has a surface porosity of at least about 1 volume percent and a surface roughness of at least 10 microns Ra. Moreover, the interior portion includes phosphorescent paint disposed or integrated thereon for visual indication of bacteria irradiation or reduction.

The method 110 further comprises a step 116 of sensing the occupant zone to determine whether the occupant zone is unoccupied. By way of the sensor 50 or a plurality thereof, input data is communicated to the processor 46 for determining the occupancy status in the occupancy zone. In one embodiment, the sensor 50 may be a motion sensor to thereby sense movement or motion within the occupancy zone. Such input data may be communicated to the processor.

The method 110 further comprises a step 120 of enabling a high energy visible (HEV) light source, if the occupant zone is determined to be unoccupied based on input data from the sensor 50 and other data. Based on the input data, the processor 46 may enable or disable the HEV light source 42 in the occupant zone 26. In one example, if no motion within the occupancy zone 26 is detected within a predetermined duration, e.g. 5 minutes, then the processor 46 may enable the HEV light source 42 within the occupant zone 26.

The method 110 further comprises a step 124 of exposing the HEV light source 42 on the interior portion 34 to irradiate bacteria from the occupant zone 26 upon enabling the HEV light source 42. As the HEV light source 42 is preferably mounted on the interior portion 34 of the occupancy zone 26, HEV light is exposed onto the surfaces of the interior portion 34 thereby irradiating or reducing bacteria therefrom. The step 124 of exposing the HEV light source 42 on the interior portion 34 may have an automated or preselected area density of energy, time duration, or any other suitable predetermined manner of ending the step 124 of exposing. In another embodiment, the duration may also be manually set without departing from the spirit of the disclosure.

The method 110 then comprises a step 130 of exciting or reacting phosphorescent paint 38 by way of the HEV light source 42 to indicate exposure of HEV light in occupant zone 26. As phosphorescent paint illuminates when exposed to HEV light, the phosphorescent paint 38 serves as an indication cue to the occupant that a bacteria irradiation/reduction process had occurred.

As discussed above, the processor 46 may include at least one algorithm having preferably but not necessarily a plurality of steps or rules to enable/disable the HEV light source 42 in the occupancy zone 26. FIG. 4 is a schematic flowchart of a control algorithm 210 for enabling and disabling the HEV light source. In this embodiment, as input data is received from the sensor 50 along with other data, the processor 46 runs the control algorithm 210 having a plurality of steps through which the processor undergoes to enable/disable the HEV light source 42. In this embodiment, at least one step involves input data from the sensor.

As shown in step 212, vehicle occupancy status is assessed. If the vehicle 10 is occupied, then HEV light source 42 is or remains disabled. If the vehicle 10 is unoccupied, then door lock status is assessed in step 216. In this example, if the vehicle doors are unlocked, then the HEV light source 42 is or remains disabled. If the doors are locked, then vehicle windows are assessed in step 220. In this example, if the windows are open, then the HEV light source 42 is or remains disabled. If the windows are closed, then vehicle battery charge is assessed in step 224. If the vehicle battery charge level is lower than a predetermined threshold, then the HEV light source 42 is or remains disabled. In this example, if the vehicle battery charge level is at or higher than the predetermined threshold, then the HEV light source 42 is enabled.

It is also to be understood that the algorithm steps discussed herein may be reduced or modified as needed. Moreover, additional algorithm steps employing additional assessments and rules may be implemented as desired. Such additional assessments may, but are not limited to, include engine run status, window open/close status, vehicle battery charging status (for electric vehicles), vehicle parked status, and vehicle temperature status. For example, steps of the algorithm may include assessing an open window status and closing the window if the window is assessed to be in open.

Bacterial reduction testing was performed using a modified ASTM E1153 test method. 405 nm light was tested against *Staphylococcus aureus* bacteria deposited on test surfaces from a 0.1% Triton-X-100 (Octyl phenol ethoxylate) surfactant solution dried on sanitized automotive surfaces.

The automotive surfaces tested were thermoplastic olefin (TPO), painted polypropylene, leather, woven foam-backed fabric, and seating vinyl. Such leather and fabric surfaces are porous. When bacteria come into contact with porous surfaces, bacteria can enter the pores which will be shielded from incident light. If bacteria are in a liquid, the liquid can flow into the pores. The vinyl sample is textured with a leather like grain. Bacteria can be partially shielded from incident light in the rough surface morphology.

As leather has a porosity of between about 0.04 and about 0.53 mL of open space per gram of leather and has a density of about 0.86 g/cm$^3$, leather can then be determined to have a porosity of about (0.04/0.86) to about (0.53/0.86) which may be found to be about 24 to about 62 vol % porosity.

FIG. 5 is a table depicting bacteria reduction data of surfaces exposed by selected cumulative energy levels from a high energy light source. The cumulative energy levels shown were 5 J/cm$^2$, 20 J/cm$^2$, and 40 J/cm$^2$. The surfaces exposed were TPO (thermoplastic olefin), painted PP (polypropylene), leather, fabric, and vinyl. As provided, the data shows the expected dose-response relationship of greater energy doses resulting in increased bacterial reduction. An exception is fabric after 40 J/cm$^2$, which likely results from shading of bacteria under woven fibers. The reduction of bacterial populations on leather and fabric show that blue light can kill bacteria in porous surfaces. The reduction of bacterial populations on vinyl shows that blue light can kill bacteria in textured soft surfaces. All numbers are an average of three samples and represent the reduction in population compared to 0 J/cm² control samples.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. A system for bacteria irradiation from a defined zone, the system comprising:
    a vehicle comprising:
        an interior portion disposed in the occupant zone, the interior portion having a surface, a predetermined surface porosity and a predetermined surface roughness, the predetermined surface porosity being of at least about 1 volume percent and the surface roughness being of at least 10 microns Ra, the interior portion having phosphorescent paint for visual indication of bacteria irradiation;
        a high energy visible (HEV) light source integrated within the interior portion and mounted flush with the surface of the interior portion, the HEV light source having an emission wavelength of between about 390 nm and about 410 nm, the HEV light source providing a cumulative energy of between about 5 J/cm² and about 40 J/cm²;
        a vehicle processor in communication with the HEV light source, the vehicle processor configured to enable the HEV light source; and
        a sensor in communication with the vehicle processor and configured to provide input on when to enable the HEV light source.

2. The system of claim 1 wherein the interior portion has surface porosity of at least about 0.5 area percent.

3. The system of claim 1 wherein the HEV light source is a light-emitting diode.

4. The system of claim 1 wherein the emission wavelength of the HEV light source is between about 400 nm and about 405 nm.

5. The vehicle of claim 1 wherein the cumulative energy of the HEV light source is about 20 J/cm².

6. The vehicle of claim 1 wherein the sensor includes a motion sensor, a mass sensor, an ultrasonic sensor, a pressure sensor, an optical sensor, a light sensor, a temperature sensor, and an infrared sensor.

7. The system of claim 1 wherein the interior portion includes an instrument panel, door trim, seating, a headliner, an overhead trim, consoles, cargo trim, steering wheel, flooring systems, displays, buttons, and switches.

8. A vehicle having a system for bacteria irradiation, the vehicle comprising:
    a chassis;
    a body supported by the chassis, the body including a motor compartment and an occupant zone; and
    a system for bacteria irradiation from the occupant zone, the system for bacteria irradiation comprising:
        an interior portion disposed in the occupant zone, the interior portion having a surface and a surface porosity of at least about 1 volume percent and a surface roughness of at least 10 microns Ra, the interior portion having phosphorescent paint for visual indication of bacteria irradiation;
        a high energy visible (HEV) light source integrated within the interior portion and mounted flush with the surface of the interior portion, the HEV light source being a light-emitting diode and having an emission wavelength of between about 390 nm and about 410 nm, the HEV light source providing a cumulative energy of between about 5 J/cm² and about 40 J/cm²;
        a vehicle processor in communication with the HEV light source, the vehicle processor configured to enable the HEV light source; and
        a sensor in communication with the vehicle processor and configured to provide input on when to enable the HEV light source.

9. The vehicle of claim 8 wherein the interior portion includes an instrument panel, door trim, seating, a headliner, an overhead trim, consoles, cargo trim, steering wheel, flooring systems, displays, buttons, and switches.

10. The vehicle of claim 8 wherein the emission wavelength of the HEV light source is between about 400 nm and about 405 nm.

11. The vehicle of claim 8 wherein the cumulative energy of the HEV light source is about 20 J/cm².

12. The vehicle of claim 8 wherein the sensor includes one of a motion sensor, a mass sensor, an ultrasonic sensor, a pressure sensor, an optical sensor, a light sensor, a temperature sensor, and an infrared sensor.

13. The vehicle of claim 8 wherein the interior portion has surface porosity of at least about 0.5 area percent.

14. A method of irradiating bacteria from an occupant zone of a vehicle, the method comprising:
    providing an interior portion disposed in the occupant zone, the interior portion having a surface, a surface porosity of at least about 1 volume percent, and a surface roughness of at least 10 microns Ra, the interior portion having phosphorescent paint for visual indication of bacteria irradiation;
    providing a high energy visible (HEV) light source integrated within the interior portion and mounted flush with the surface of the interior portion, the HEV light source being a light-emitting diode and having an emission wavelength of between about 390 nm and about 410 nm, the HEV light source providing a cumulative energy of between about 5 J/cm² and about 40 J/cm²;
    sensing the occupant zone to determine whether the occupant zone is unoccupied;
    enabling a high energy visible (HEV) light source, if the occupant zone is determined to be unoccupied;
    exposing the HEV light source on the interior portion to irradiate bacteria from the occupant zone; and
    reacting phosphorescent paint to HEV light source to indicate exposure of HEV light source in occupant zone.

* * * * *